(12) United States Patent
Skinner et al.

(10) Patent No.: US 6,374,142 B1
(45) Date of Patent: Apr. 16, 2002

(54) ISODIAMETRIC PACING/DEFIBRILLATION LEAD

(75) Inventors: Dwight Skinner, St. Anthony; Chris Knapp, Oakdale, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/510,422

(22) Filed: Feb. 22, 2000

(51) Int. Cl.[7] .................................................. A61N 1/04
(52) U.S. Cl. ...................................................... 607/122
(58) Field of Search ................................ 607/122, 123, 607/119

(56) References Cited

U.S. PATENT DOCUMENTS

| | | | |
|---|---|---|---|
| 4,161,952 A | 7/1979 | Kinney et al. | 128/786 |
| 4,559,951 A | 12/1985 | Dahl et al. | 128/642 |
| 4,934,049 A | 6/1990 | Kiekhafer et al. | 29/883 |
| 5,014,720 A | 5/1991 | Barcel et al. | 128/786 |
| 5,115,818 A | 5/1992 | Holleman et al. | 128/784 |
| 5,347,708 A | 9/1994 | Bischoff et al. | 29/825 |
| 5,552,872 A | 9/1996 | Hoff | 607/119 |
| 5,609,621 A | 3/1997 | Bonner | 607/122 |
| 5,649,974 A | 7/1997 | Nelson et al. | 607/122 |
| 5,755,762 A | 5/1998 | Bush | 607/122 |

Primary Examiner—Scott M. Getzow
(74) Attorney, Agent, or Firm—Nikolai & Mersereau, P.A.

(57) ABSTRACT

A joint for a cardiac stimulation lead is disclosed that connects a lead body and a coil conductor with an isodiametric junction. The lead body includes a counterbore disposed at its distal end. The lead body's counterbore securably receives the inner insulator of the coil conductor. Alternatively, the coil conductor includes a counterbore disposed at its proximal end. The coil conductor's counterbore securably receives the distal end of the lead body.

28 Claims, 3 Drawing Sheets

ISODIAMETRIC PACING/DEFIBRILLATION LEAD

FIELD OF INVENTION

The present invention relates to implantable medical leads, and more particularly implantable pacing/defibrillation leads for applications such as cardiac pacemaking or cardioversion, including heart stimulation and monitoring.

BACKGROUND OF INVENTION

Implantable leads can be used to pass an electric current through the myocardium to alleviate arrhythmias, for example using the methods of cardioversion for tachycardia, defibrillation for ventricular fibrillation, and other methods depending on the particular arrhythmia. Alleviation of arrhythmias can be accomplished transvenously by implanting leads in the heart. The implantable leads form an electrical connection between a pulse generator or other electronic device and the heart.

Leads typically include one or more electrodes at the lead's distal end. The electrodes are designed to form an electrical connection with a tissue or organ. A flexible conductor electrically connects the electrode to the pulse generator. Commonly, the flexible conductor takes the form of a single or multifilar wire coil. Although, stranded or solid cables are also used. Regardless of the form, an insulating layer of material typically surrounds the flexible conductors. Together, the flexible conductor and the insulating layer form the lead body. The lead body electrically and mechanically couples the pulse generator at its proximal end to the electrode at its distal end.

Transvenous cardioversion and defibrillation leads employ cardioversion and defibrillation electrodes, respectively. These electrodes are typically configured as elongated metal coils. Transvenous pacing leads, cardiac ablation catheters and other electrode bearing leads and catheters may also employ coil electrodes. Leads having coil electrodes are commonly manufactured by winding the wire into a helix around the exterior surface of the lead body. The winding of wire around the lead body typically creates a region of increased diameter relative to the lead body. The increased diameter is usually twice the wire's diameter. Alternatively, a lead body may be attached to a separate coil electrode. A collar or transition is typically provided at the juncture of the lead body and a separate coil electrode. The collar or transition mechanically stabilizes the junction between the lead body and the separate coil electrode. The collar or transition also typically creates a region of increased diameter. The increased diameter resulting from the above methods is detrimental to the patient because they require an increased diameter introducer for implantation. The use of an increased diameter introducer increases the trauma to tissues during implantation. The increased diameter introducer also limits the size of the vein in which the electrode may be introduced. In addition, the collar or transition complicates the explanting of the lead by potentially "hanging-up" on a removal sheath used for this purpose and thereby, increases the risk to the patient. Alternatively, if no sheath is used, a danger of having the collar or transition "hanging-up" on fibrotic tissue exists during explanting. Thus, there is a need to provide a coil electrode having a uniform diameter junction with the lead body to produce an isodiametric lead.

The present invention meets the above needs and provides additional advantages and improvements that will be evident to those skilled in the art.

SUMMARY OF THE INVENTION

The present invention provides a lead that is substantially isodiametric over the region where the lead body transitions to coiled electrode. The present invention eliminates the need to use an increased diameter introducer to allow passage of a lead's region of increased diameter and reduces or eliminates the possibility of a region of increased diameter creating a shoulder capable of "hanging-up" on the introducer, removal sheath or fibrotic tissue during implanting and explanting.

The lead includes a lead body and a coil electrode. The lead body includes at least one conductor and an elongated, flexible polymeric lead insulator surrounding the conductor. The lead body may also include additional pacing and/or sensing conductors. The individual conductors may be single wires or a plurality of wires. The lead insulator generally defines an outside diameter, an internal lumen and a counterbore at its distal end. The coil electrode includes a wire wound as a helix around an inner insulator. The inner insulator can define one or more additional lumens. The coil electrode has a coil diameter substantially equal in size to the outside diameter of the lead insulator. The coil electrode is electrically coupled to the conductor. The wire helix may be electrically coupled to the conductor by spirally winding the shocking coil around the shocking conductor, welding, crimping or a conductive adhesive. The inner insulator is secured within the counterbore of the lead insulator. The inner insulator may be frictionally secured, adhesively bonded or welded within the counterbore of the lead insulator. If the lead body has additional pacing or sensing conductors, a distal end of the pacing or sensing conductors extending distally beyond the counterbore in the distal end of the lead insulator and into the lumen of the inner insulator. Thereby, the lead insulator and the inner insulator continuously electrically insulate the pacing and/or sensing conductors from the coil electrode.

Alternatively, the inner insulator of the coil electrode defines the counterbore at its proximal end instead of the lead body defining a counterbore at its distal end. In this later embodiment, the lead insulator is secured within the counterbore of the inner insulator. Again, the lead insulator may be frictionally secured, adhesively bonded or welded within the counterbore of the inner insulator.

DETAILED DESCRIPTION OF THE INVENTION

Figure 1:
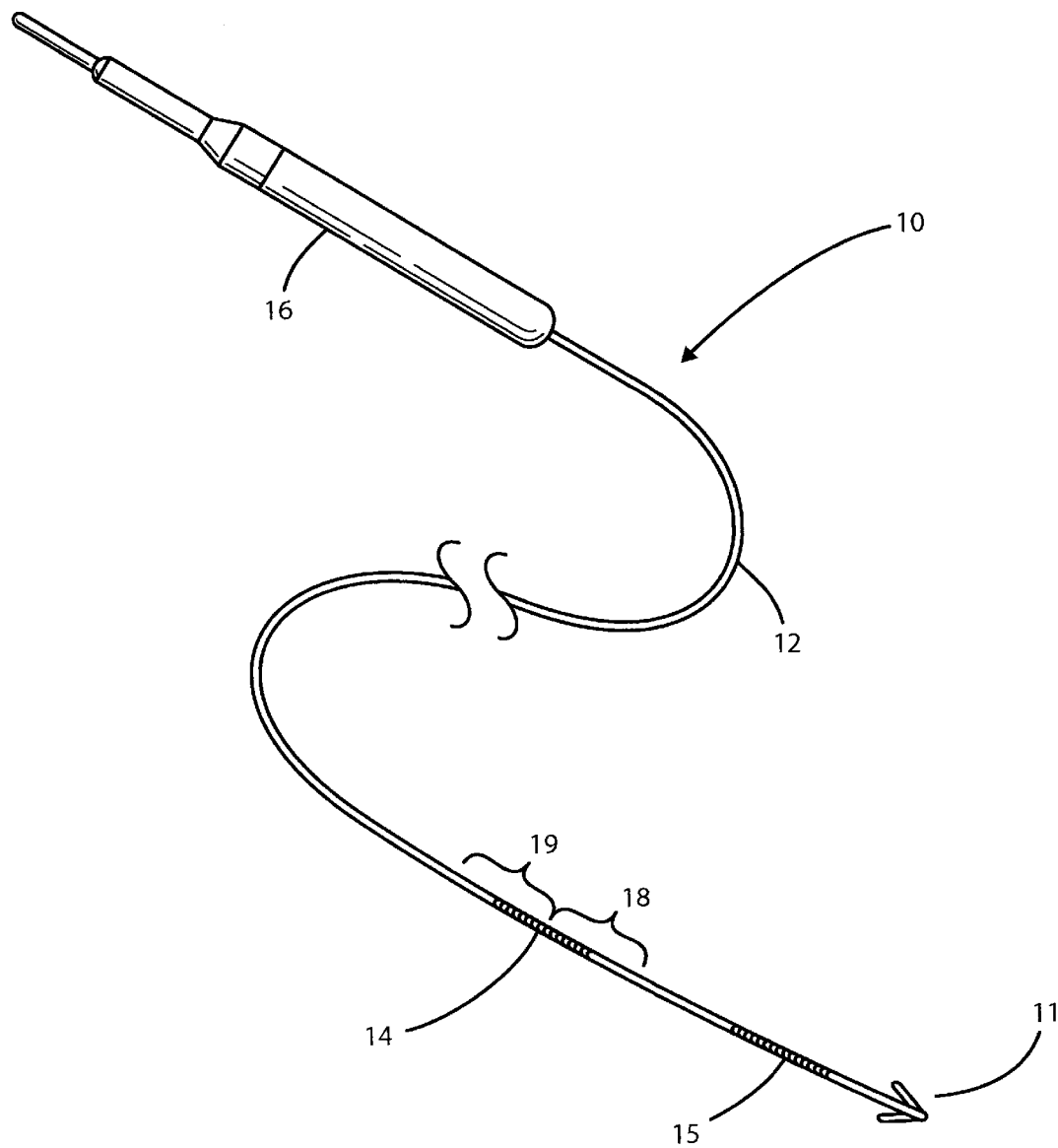
FIG. 1 illustrates a plan view of an embodiment for an isodiametric cardioversion/defibrillation lead in which an embodiment of the present invention is practiced.

The present invention is applicable to a variety of implantable medical devices for providing an electric current to selected body tissues or transmitting signals from a sensing electrode to the medical device. The invention is described in the context of a defibrillation or cardioversion electrode designed for transvenous implantation. The appended claims are not intended to be limited to any specific example or embodiment described in this patent. It will be understood by those skilled in the art that the present invention may be used to secure electrodes to lead bodies to produce a wide variety of leads including, but not limited to, sensing leads, pacing leads, defibrillation leads, and other medical leads both unipolar and multipolar. Further, in the drawings described below, reference numerals are generally repeated where identical elements appear in more than one figure.

FIG. 1 illustrates an embodiment of a lead 10 made in accordance with the present invention. Lead 10 includes a lead body 12, a coil electrode 14, a second coil electrode 15, a tip electrode 11 and a lead connector pin 16. Lead 10 is generally configured to transmit an electric signal from a pulse generator (not shown) to the heart. Further, lead 10 is configured to permit insertion through a selected vein and the guiding of the electrodes to a target locations in or on the heart. Typically, lead body 12 is a flexible, elastomeric structure round in cross-section, but could be any number of materials, sizes and shapes appropriate for specific applications. The pulse generator may be a cardiac rhythm management device, such as a cardioverter/defibrillator, a pacemaker, or a sensing/diagnostic instrument. Lead connector pin 16 is provided at the proximal end of lead body 12. Lead connector pin 16 is configured to form an electrical connection with the cardiac rhythm management device. Typically, the lead connector pin conforms to the international standard IS-1 when used to connect a lead to a pacemaker, although, it could take any number of forms known to those skilled in the art.

Figure 2:
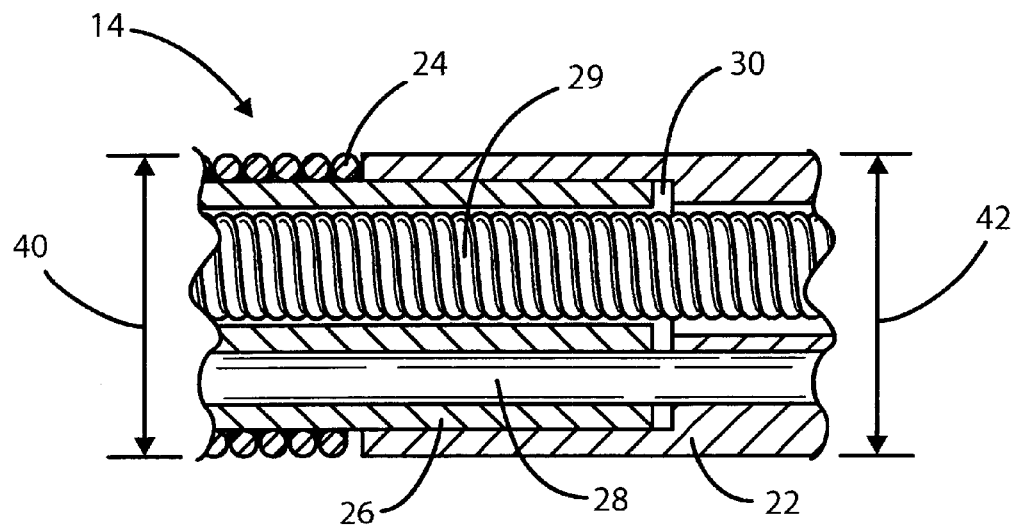
FIG. 2 illustrates a greatly enlarged sectional side view showing an embodiment of the connection between the distal end of the coil electrode and the proximal end the lead body of the lead of FIG. 1.
Figure 3:
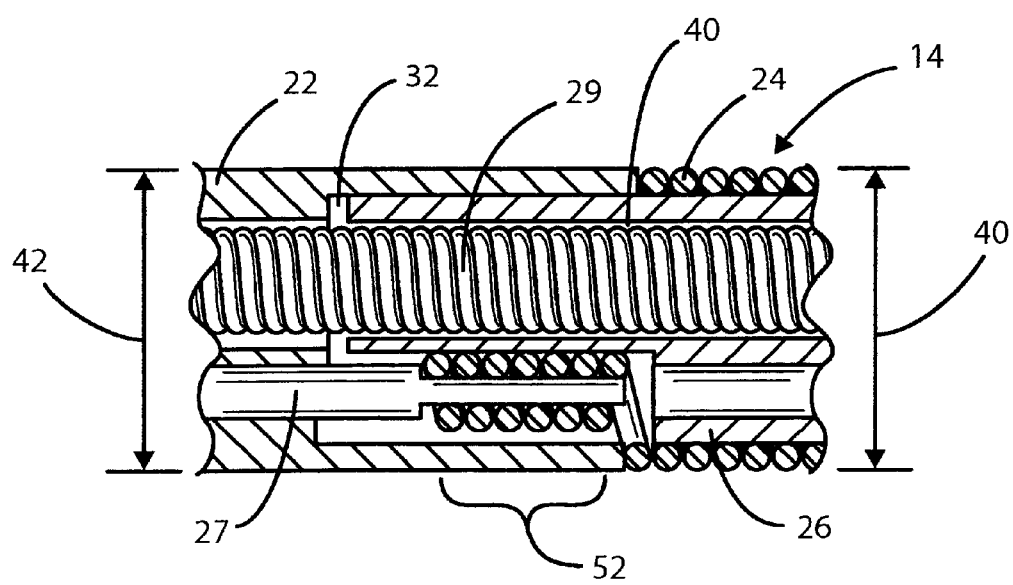
FIG. 3 illustrates a greatly enlarged sectional side view showing an embodiment of the connection between the proximal end of the coil electrode and the distal end of the lead body of the lead of FIG. 1.
Figure 4:
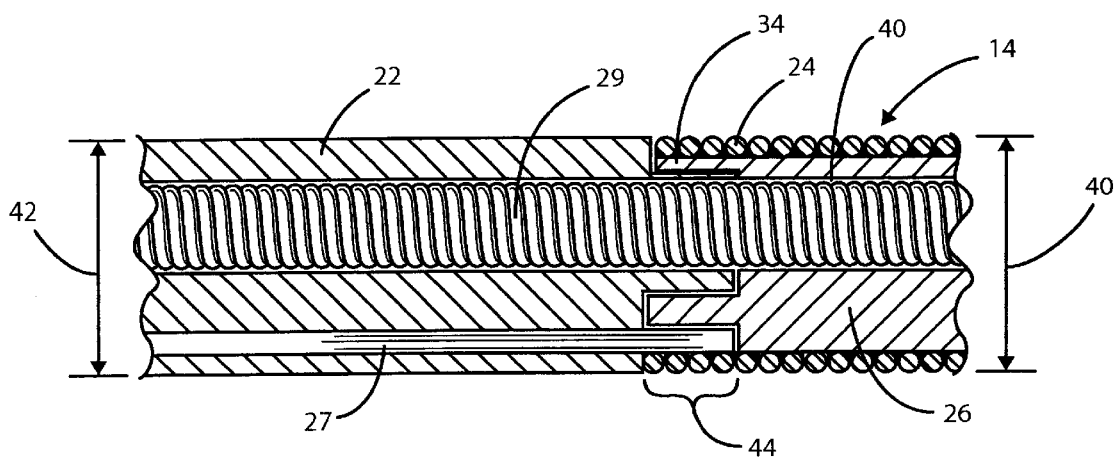
FIG. 4 illustrates a greatly enlarged sectional side view showing another embodiment of the connection between the proximal end of the coil electrode and the distal end of the lead body of the lead of FIG. 1.

FIG. 2 and FIGS. 3 and 4 illustrate the details alternative embodiments of region 18 and region 19 in FIG. 1, respectively. Lead body 12 includes a flexible polymeric lead insulator 22 surrounding at least one defibrillating conductor 28 and at least one pacing conductor 29. In the embodiment of FIG. 1, a defibrillating conductor 27, shown in FIGS. 3 and 4, is electrically coupled to defibrillating electrode 14 and a second defibrillating conductor 28, shown in FIG. 2, is electrically coupled to second defibrillating electrode 15. Lead insulator 22 is generally configured to insulate the conductors and present a smooth biocompatible external surface to body tissues. Thus, lead insulator 22, either alone or in combination with an inner insulator 26, described below, is typically coextensive with the conductors. The material of lead insulator 22 is typically selected based on biocompatibility, biostability and durability for the particular application. Lead insulator 22 may be silicone, polyurethane, polyethylene, polyimide, PTFE, ETFE, or other materials known to those skilled in the art. Typically, the conductors are in the form of a cables and/or coils. The cable or coil may be made up of one or more conductive wires or filars. The conductors may be composed of stainless steel, MP35N, drawn-brazed-strand (DBS), platinum alloy, or other conductive materials known to those skilled in the art. The number, size, and composition of the conductors will depend on particular application for the lead. Regardless of the conductors used, lead body 12 should be capable of readily conforming to the irregular passageways and shapes of the cardiovascular system. Accordingly, the lead body should have enough flexibility to permit the lead body to flex easily, and elastically.

Coil electrodes 14 and 15 are provided near the distal end of lead body 12. To stimulate the heart, coil electrode 14 and 15 may be positioned within the right atrium or right ventricle, or at other positions within or on the heart appropriate for particular applications. Coil electrodes 14 and 15 typically include a wire 24 wound as a helix around an inner insulator 26. Wire 24 may be composed of a biocompatible conducting material, such as stainless steel, MP35N, DBS, platinum allow or other electrically conductive materials known to those skilled in the art. Wire 24 is electrically connected to conductors 27 and 28 when used in coil electrodes 14 and 15, respectively. The electrical connection can be a weld, by crimping, by an electrically conductive adhesive, by intertwining the conductor and the wire or by other methods known to those skilled in the art. Inner insulator 26 provides the framework around which the wire is wound and, in addition, can electrically isolate conductors 28 and 29 that typically extend through lumen distally beyond the defibrillation conductor 27. Thus for purposes of the present invention, although inner insulator 26 typically functions as an insulator, it is not necessary for inner insulator 26 to function as an insulator. Inner insulator 26 may function solely as a structure on which wire 24 is wound to forming a coil electrode or alternatively, as a structure on which a pre-wound wire 24 is placed to define a structure for connecting the coil electrode to the lead body. Inner insulator 26 is typically coextensive with wire 24, although it can extend proximally and/or distally beyond wound wire 24 as appropriate for a particular application. Inner insulator 26 may be made from a variety of materials including silicone, polyurethane, polyethylene, polyimide, PTFE, ETFE, or other materials known to those skilled in the art. Inner insulator 26 is typically selected based on biocompatibility, biostability and durability. Inner insulator 26 is generally configured to receive wire 24 such that the shape and coil diameter 40 of the wound wire is substantially corresponds the shape and outside diameter 42 of the lead body's insulator.

FIG. 2 illustrates the details of an embodiment of the junction between a proximal end of lead body 12 and a distal end of coil electrode 14 within region 18 of FIG. 1. The embodiment of FIG. 2 joins the proximal end of lead body 12 to the distal end of coil electrode 14 by inserting inner insulator 26 into a counterbore 30 in lead insulator 22 at the proximal end of lead body 12. Counterbore 30 can be mechanically cut, integrally molded or formed by other means known to those skilled in the art within the proximal end of lead body 22. Inner insulator 26 has its distal end dimensioned to fit within counterbore 30 at the proximal end of lead insulator 22 such that inner insulator 26 may be secured in counterbore 30. Inner insulator 26 is typically secured within counterbore 30 using an appropriate adhesive for the materials and application. Alternatively, inner insulator 26 could be secured within counterbore 30 by friction, welding, or thermal or chemical bonding of the insulators with one another, or by configuring the distal end of inner insulator 26 and counterbore 30 to mechanically interlock. The embodiment of FIG. 2 shows second defibrillating conductor 28 and pacing conductor 29 extending beyond coil electrode 14 to second coil electrode 15 and tip electrode 1, respectively.

FIG. 3 illustrates details of an embodiment of the junction between a distal end of lead body 12 and a proximal end of coil electrode 14 within region 19 of FIG. 1. The embodiment of FIG. 3 joins the distal end of lead body 12 to the proximal end of coil electrode 14 by inserting inner insulator 26 into a counterbore 32 in lead insulator 22 at the distal end of lead body 12. Counterbore 32 can be mechanically cut, integrally molded or formed by other means known to those skilled in the art within the distal end of lead body 22. Inner insulator 26 has its proximal end dimensioned to fit within counterbore 32 at the distal end of lead insulator 22 such that inner insulator 26 may be secured in counterbore 32. Inner insulator 26 is typically secured within counterbore 32 using an appropriate adhesive for the materials and application. Alternatively, inner insulator 26 could be secured within counterbore 32 by friction, welding, or thermal or chemical bonding of the insulators with one another, or by configuring the proximal end of inner insulator 26 and counterbore 32 to mechanically interlock. The embodiment shows the electrical connection of conductor 27 to the wire 24 over a wound region 52 wherein wire 24 is wound around conductor 28. Alternatively, conductor 28 can be wound around wire 24 or other methods of electrically connecting discussed above could be used.

FIG. 4 illustrates details of another embodiment of the junction between a distal end of lead body 12 and a proximal end of coil electrode 14 within region 19 of FIG. 1. The particular embodiment joins lead body 12 to coil electrode 14 by inserting a reduced diameter portion at the distal end of lead body 12 into a counterbore 34 in the proximal end of inner insulator 26. Counterbore 34 can be mechanically cut, integrally molded or formed by other means known to those skilled in the art within the proximal end of inner insulator 26. The distal end of lead insulator 22 is adapted to fit within counterbore 34 at the proximal end of coil electrode 14 such that inner insulator 26 may be secured in counterbore. The distal end of lead insulator 22 is typically secured within counterbore 34 using an appropriate adhesive for the materials and application. Alternatively, lead insulator 22 could be secured within counterbore 34 by welding, thermal or chemical bonding of the insulators with one another, or by configuring the proximal end of lead insulator 22 and counterbore 34 to mechanically interlock. The embodiment shows the electrical connection of conductor 27 to the wire 24 over a wound region 44 wherein wire 24 is wound around conductor 28 and inner insulator 26 bringing wire 24 into contact with conductor 27. Alternatively, the other methods of electrically connecting conductor 27 to wire 24 discussed above could be used.

As noted above, the use of a defibrillation/pacing electrode as described herein is for exemplary purposes only. It will be understood by those skilled in the art how to apply the present invention to a variety of medical leads.

What is claimed is:

1. A lead, comprising:
    a lead body including at least one conductor and a lead insulator surrounding the conductor, the lead insulator having an outside diameter;
    a coil electrode comprising a wire wound around an inner insulator, the coil electrode having a coil diameter substantially the same as the outside diameter of the lead insulator, and wherein one of the inner insulator and the lead insulator define a counterbore and the inner insulator and the lead insulator are connected by the counterbore such that the lead body and the coil electrode are substantially longitudinally coaxial.

2. A lead, as in claim 1, wherein the counterbore is disposed at a distal end of the lead body and the inner insulator is secured within the counterbore to connect the coil electrode and the lead body.

3. A lead, as in claim 1, wherein the counterbore is disposed at a proximal end of the inner insulator and the lead body is secured within the counterbore to connect the lead body and the coil electrode.

4. A lead, as in claim 1, wherein the conductor is a single wire.

5. A lead, as in claim 1, wherein the conductor is a plurality of wires.

6. A lead, as in claim 1, wherein the counterbore frictionally secures the inner insulator to the lead body.

7. A lead, as in claim 1, wherein the inner insulator is adhesively bonded to the lead insulator.

8. A lead, as in claim 1, wherein the inner insulator is thermally bonded to the lead insulator.

9. A lead, as in claim 1, wherein the inner insulator is chemically bonded to the lead insulator.

10. A lead, as in claim 1, wherein the coil electrode is electrically coupled to the conductor.

11. A lead, as in claim 10, wherein the wire is electrically coupled to the conductor by spirally winding the wire around the conductor.

12. A lead, as in claim 10, wherein the wire is electrically coupled to the conductor by welding.

13. A lead, as in claim 10, wherein the wire is electrically coupled to the conductor by crimping.

14. A lead, as in claim 10, wherein the wire is electrically coupled to the conductor by an adhesive.

15. A method for securing a lead body to a coil electrode, comprising:
    providing a lead body including a conductor and a lead insulator, and a coil electrode having an inner insulator, wherein one of the lead insulator and the inner insulator defines a counterbore; and
    securing the inner insulator and the lead insulator by the counterbore such that the lead body and the coil electrode are substantially longitudinally coaxial.

16. A method, as in claim 15, wherein the counterbore is disposed at a distal end of the lead body and the inner insulator is secured within the counterbore to connect the coil electrode and the lead body.

17. A method, as in claim 15, wherein the counterbore is disposed at a proximal end of the inner insulator and the lead body is secured within the counterbore to connect the lead body and the coil electrode.

18. A method, as in claim 15, further comprising electrically coupling the conductor to the coil electrode.

19. A method, as in claim 18, wherein electrically coupling the coil electrode to the conductor is by welding.

20. A method, as in claim 18, wherein electrically coupling the coil electrode to the conductor is by crimping.

21. A method, as in claim 18, wherein electrically coupling the coil electrode to the conductor is by an electrically conductive adhesive.

22. A method, as in claim 15, wherein securing the inner insulator within the counterbore of the lead insulator is by adhesively bonding.

23. A method, as in claim 15, wherein securing the inner insulator within the counterbore of the lead insulator is by welding.

24. A method for securing a lead body to a coil electrode, comprising:
    a step for providing lead body including a conductor and a lead insulator, and a coil electrode having an inner insulator, wherein one of the lead insulator and the inner insulator defines a counterbore; and
    a step for securing the inner insulator and the lead insulator by the counterbore such that the lead body and the coil electrode are substantially longitudinally coaxial.

25. A method, as in claim 24, further comprising a step for electrically coupling the conductor to the coil electrode.

26. A lead, as in claim 24, wherein the counterbore is disposed at a distal end of the lead body and the inner insulator is secured within the counterbore to connect the coil electrode and the lead body.

27. A lead, as in claim 24, wherein the counterbore is disposed at a proximal end of the inner insulator and the lead body is secured within the counterbore to connect the lead body and the coil electrode.

28. A stepless joint connection between a medical stimulating lead body and a surface coil electrode supported by the lead body, comprising:

(a) a first tubular insulating member including one of a male and a female coupling member, the tubular insulating member being of a first predetermined diameter;

(b) an electrical conductor of a second predetermined diameter wrapped circumferentially about the tubular insulating member; and (c) the lead body being of a third predetermined diameter and having an other of the male and female coupling member thereon so as to coaxially mate with the one coupling member of the first tubular insulating member and wherein the sum of the first and second predetermined diameters equals the third predetermined diameter.

* * * * *